United States Patent [19]

Yoshida et al.

[11] Patent Number: 5,386,122
[45] Date of Patent: Jan. 31, 1995

[54] RADIATION DETECTOR AND METHOD FOR MAKING THE SAME

[75] Inventors: Minoru Yoshida, Tokyo; Manabu Nakagawa, Kanagawa; Tomonori Yoshioka, Kashiwa, all of Japan

[73] Assignee: Hitachi Medical Corporation, Tokyo, Japan

[21] Appl. No.: 82,978

[22] Filed: Jun. 29, 1993

[30] Foreign Application Priority Data

Jun. 30, 1992 [JP] Japan .................. 4-172568

[51] Int. Cl.⁶ .................................. G01T 1/20
[52] U.S. Cl. .................. 250/368; 250/370.4
[58] Field of Search ........... 250/370.11, 368, 366, 250/367

[56] References Cited

U.S. PATENT DOCUMENTS

| | | | |
|---|---|---|---|
| 4,563,584 | 1/1986 | Hoffman et al. | 250/370.11 |
| 4,870,279 | 9/1989 | Cueman et al. | 250/370.11 |
| 4,982,095 | 1/1991 | Takahashi et al. | 250/370.11 |
| 5,276,328 | 1/1994 | Yoshida et al. | 250/370.11 |

FOREIGN PATENT DOCUMENTS

| | | | |
|---|---|---|---|
| 62-24174 | 2/1987 | Japan | 250/368 |
| 1191087 | 8/1989 | Japan . | |
| 2208591 | 8/1990 | Japan | 250/370.11 |
| 310188 | 1/1991 | Japan | 250/370.11 |

*Primary Examiner*—Paul M. Dzierzynski
*Assistant Examiner*—Drew A. Dunn
*Attorney, Agent, or Firm*—Antonelli, Terry, Stout & Kraus

[57] ABSTRACT

A radiation detector providing with a multi-channels photodiode formed on a substrate and having its individual channels isolated from each other by a plurality of channel isolation lines respectively, a scintillator cut along the channel isolation lines to be formed with a plurality of grooves into which a plurality of isolation plates isolating the individual channels from each other are inserted respectively, and a light shield coated on or bonded to each of both ends of the scintillator located in the direction of groove cutting.

20 Claims, 4 Drawing Sheets

RADIATION DETECTOR AND METHOD FOR MAKING THE SAME

BACKGROUND OF THE INVENTION

This invention relates to a multi-element radiation detector commonly used in an X-ray computed tomography for medical use and the like, and more particularly to an X-ray detector of the above type in which undesirable crosstalk between the adjacent X-ray detection elements can be prevented thereby ensuring the desired uniform spectral sensitivity while improving the industrial productivity.

A radiation detector is now widely used in an X-ray computed tomography for medical use, an X-ray scanography system or the like and is also used in a baggage inspection system or the like, and an improvement in the detection operation performance of the radiation detector is more and more demanded so as to improve the quality of reconstructed images displayed as a result of detection by the detector. Among the apparatuses described above, the Xenon ionization detector is commonly used as the X-ray detector in the X-ray computed tomography. This conventional X-ray detector is being gradually replaced now by a multi-element radiation solid-state detector (referred to hereinafter merely as a detector) capable of operating with a higher S/N ratio. FIG. 4 is a schematic perspective view showing the basic structure of the detector described above.

Referring to FIG. 4, the detector includes scintillators 1 converting incident X-ray 5 into visible light, a plurality of isolation plates 2 isolating the adjacent X-ray detection elements from each other, and a multi-channels Si photodiode 3 formed on a substrate 4 for converting the visible light emitted from the scintillators 1 into an electrical signal. The scintillators 1 are bonded to an upper surface 3a of the Si photodiode 3, and those belonging to the individual channels of the Si photodiode 3 are arranged in parallel to each other with a predetermined pitch on the substrate 4 together with the isolation plates 2 thereby forming an array of the X-ray detection elements. A plurality of light detection parts 3b are formed on the surface 3a of the Si photodiode 3 as shown.

In the detector having the structure shown in FIG. 4, the scintillators 1 convert the incident X-ray 5 into visible light having an intensity proportional to the intensity of the incident X-ray 5. While being repeatedly reflected by the surfaces of the isolation plates 2, the interfaces or surfaces of the scintillators 1, etc., the visible light produced by conversion is guided toward the light detection parts 3b of the Si photodiode 3. The visible light is subjected to photoelectric conversion at the light detection parts 3b to be detected as an electrical signal (photocurrent) having the strength proportional to the intensity of the light supplied from the scintillators 1.

It is well known that whether the optical characteristic of such a detector is satisfactory or not depends mainly upon the S/N ratio as well as the spatial resolution, and the S/N ratio is determined by the efficiency of conversion of the incident X-ray 5 into its output signal, that is, the quantum efficiency. In order to improve this quantum efficiency, it is necessary to improve the light collection efficiency of the scintillators 1, to improve the photoelectric conversion efficiency of the Si photodiode 3, to improve the X-ray spatial efficiency that is the X-ray quantum efficiency of the detector, and also to improve the light transmission efficiency inside the detector.

Among the efficiencies described above, the quantum efficiency can be improved by minimizing the area of the region, such as, the space which is occupied by the individual isolation plates 2 and does not contribute to the detection of the incident X-ray 5, that is, the region except that occupied by the scintillators 1. Further, the light transmission efficiency inside the detector can be improved by minimizing both the absorption of light in the scintillators 1 themselves and the absorption of light by the surfaces of the isolation plates 2, so that the light emitted from the scintillators 1 can be efficiently guided toward the Si photodiode 3.

On the other hand, the spatial resolution of a reconstructed image in the X-ray computed tomography using the detector depends on the distance between the adjacent isolation plates 2 shown in FIG. 4, that is, the width of each of the X-ray detection elements forming the detector, and it is the recent tendency that this width of each X-ray detection element is selected to be less than 1 mm in many cases. When the width of each X-ray detection element is reduced as described above, the quantity of the X-ray 5 incident on each of the detection elements decreases to a level lower than the level of the output signal from the detection elements, resulting in an undesirable decrease of the S/N ratio. In addition, the light emitted from each of the scintillators 1 tends to be partly absorbed by the scintillator 1 itself and tends also to be repeatedly reflected in various directions by the surfaces of the scintillator 1 and the associated isolation plate 2 and also at the both ends 21 of the scintillator 1 located in the direction of cutting, etc., with the result that the proportion of direct arrival of the light incident on the Si photodiode 3 is decreased to lower the light transmission efficiency described above. In this case, the light reflectivity of each detection element especially at the both ends 21 of each scintillator 1 located in the direction of cutting cannot be made constant, with the result that undesirable crosstalk tends to occur between the adjacent detection elements. Thus, it is inevitable that the detection elements have optical characteristics different from each other.

Therefore, the individual detection elements have respectively different spectral sensitivities. As a result, in an X-ray computed tomography of third generation that employs a rotate-rotate method according to which a radiation source and a radiation detector rotate together, a ring artifact tends to appear on a reconstructed image.

An idea for controlling the reflection of light at the both ends 21 of each scintillator 1 located in the direction of cutting is proposed in, for example, JP-A-1-191087. The disclosure of the application includes the steps of polishing the surfaces of the scintillator 1 into the state of specular reflection, coating a thin transparent film of a material, such as, a resin on the five surfaces except the surface engaged by an associated light detection element, and forming a light reflective film on the surface of the resin film by vacuum evaporation or like means, for the purpose of maintaining constant the state of light reflection and improving the efficiency of light reflection. Thus, the light emitted from the scintillator 1 can be concentrated on the surface engaged by the associated light detection element so as to effectively utilize the light.

In the case of the structure disclosed in JP-A-1-191087 cited above, effective utilization of light and suppression of crosstalk in one light detection element can be attained However, it is technically difficult to ensure that the same surface state can be satisfactorily optically reproducibly maintained for the individual scintillators 1 at all times. Especially, it is technically extremely difficult to form the light reflective film, under the same condition and simultaneously, on the five surfaces of each scintillator 1 except the surface engaged by the associated light detection element. Thus, the light reflective film is practically separately formed on each of the individual scintillators 1, with the result that an undesirable fluctuation occurs inevitably between the optical characteristics of the individual light detection elements.

Further, the resin or like light reflective film formed on the five surfaces of each scintillator 1 except the surface engaged by the associated light detection element is generally inferior in its radiation durability to inorganic materials and tends to be peeled off or discolored when it is exposed to radiation for a long time. Thus, such a problem has been commonly encountered in which an undesirable ring artifact tends to appear due to the tendency of occurrence of fluctuation of the optical characteristics between the light detection elements with lapse of time.

Further, because of the fact that a modern X-ray computed tomography uses a multi-element radiation detector including as many as 1000 light detection elements, it is difficult to form all the light detection elements so that they have the same optical characteristics, and, because of an inevitable fluctuation of their optical characteristics, appearance of an undesirable ring artifact cannot be avoided. Also, many optical processing steps are required for the formation of the light detection elements. Thus, such another problem arises that the industrial productivity of the detector is low.

Furthermore, because the individual scintillators are separately manufactured as described above, it is necessary that the separately manufactured scintillators are to be precisely arranged on the Si photodiode during the process of assembling the detector. However, it is quite difficult to precisely and uniformly arrange so many scintillators on the Si photodiode, with the result that not only the industrial productivity is lowered, but also non-uniform precision leads to a fluctuation of the optical characteristics of the light detection elements. Thus, this leads to such another problem that the quality of a reconstructed image is inevitably degraded.

SUMMARY OF THE INVENTION

With a view to solve the prior art technical problems described above, it is an object of the present invention to provide a radiation detector in which undesirable crosstalk between adjacent detection elements can be prevented so as to make uniform the spectral sensitivity and to improve the industrial productivity and, also to provide a method for making the same.

The present invention which attains the above object provides a radiation detector in which, before a scintillator in plate form is cut into a plurality of detection elements by grooves, a light shield is coated on or bonded to each of both ends of the scintillator located in the direction of cutting to form the plural detection elements.

The material of this light shield has its light reflectivity lower than 30%, and a variation of this reflectivity is less than 20% in a light wavelength range of 400 nm to 900 nm. Especially, it is preferable that the reflectivity of the light shield is lower than 5%, and the variation of the reflectivity in the light wavelength range of 400 nm to 900 nm is less than 10%.

The radiation detector according to the present invention is manufactured by one of the following methods:

Manufacturing method 1

(1) A light shield in strip form is bonded to each of both ends of a scintillator in plate form located in the direction of groove cutting.

(2) The plate-form scintillator having the light shield bonded to each of its both ends is bonded to an upper surface of a multi-channels photodiode.

(3) Isolation plate insertion grooves extending along longitudinal lines isolating the individual channels of the photodiode are formed on all of the light shields, the plate-form scintillator and the photodiode.

(4) Isolation plates are inserted into the respective insertion grooves.

(5) The isolation plates are fixed to the ends of the scintillator by an adhesive.

Manufacturing method 2

(1) A scintillator in plate form is bonded to an upper surface of a multi-channels photodiode.

(2) A light shield in resin form is coated on each of both ends of the scintillator located in the direction of groove cutting.

(3) After the material of the light shields is cured, isolation plate insertion grooves extending along longitudinal lines isolating the individual channels of the photodiode are formed on all of the light shields, the plate-form scintillator and the photodiode.

(4) Isolation plates are inserted into the respective insertion grooves.

(5) The isolation plates are fixed to the ends of the scintillator by an adhesive.

Manufacturing method 3

(1) A first light shield is coated on each of both ends of a scintillator in plate form located in the direction of groove cutting.

(2) The plate-form scintillator having the first light shield coated on each of its ends is bonded to an upper surface of a multi-channels photodiode.

(3) A second light shield in resin form is coated on each of the both ends of the scintillator located in the direction of groove cutting.

(4) After the material of the second light shields is cured, isolation plate insertion grooves extending along longitudinal lines isolating the individual channels of the photodiode are formed on all of the light shields, the plate-form scintillator and the photodiode.

(5) Isolation plates are inserted into the respective insertion grooves.

(6) The isolation plates are fixed to the ends of the scintillator by an adhesive.

Because of such a construction of the detector according to the present invention, undesirable leakage of light at the both ends of the scintillator located in the direction of groove cutting can be prevented so that undesirable crosstalk between the adjacent light detection elements can be prevented. For the purpose of preventing the crosstalk, the scintillator having the coated or bonded light shields is integrally bonded to the upper surface of the photodiode, and channel isolation grooves are cut on the assembly consisting of the scintillator and the photodiode along the channel isolation lines in such a relation that each of the grooves passes the corresponding channel isolation line. Therefore, any relative dimensional difference and position deviation do not exist among the light shields, the scintillator and the photodiode, so that the undesirable crosstalk between the adjacent light detection elements can be more reliably prevented.

Also, because reflection of light at the both ends of the scintillator located in the direction groove cutting can be prevented, the reflectivities at the both ends of the scintillator can be controlled to be maintained at the same constant value, and the prior art tendency of fluctuation of the spectral sensitivities of the individual light detection elements attributable to the difference of the reflectivities at those ends can be eliminated, so that the possibility of appearance of the undesirable ring artifact can be minimized.

Further, the above manner of groove cutting is advantageous in that both the dimensional precision and the positional precision can be improved and can also be made uniform. Therefore, not only an undesirable fluctuation of the optical characteristics of the individual light detection elements can be prevented, but also the detector assembling process requiring the high degree of precision can be dispensed with, thereby improving the industrial productivity of the detector.

DESCRIPTION OF THE PREFERRED EMBODIMENTS

Figure 1:
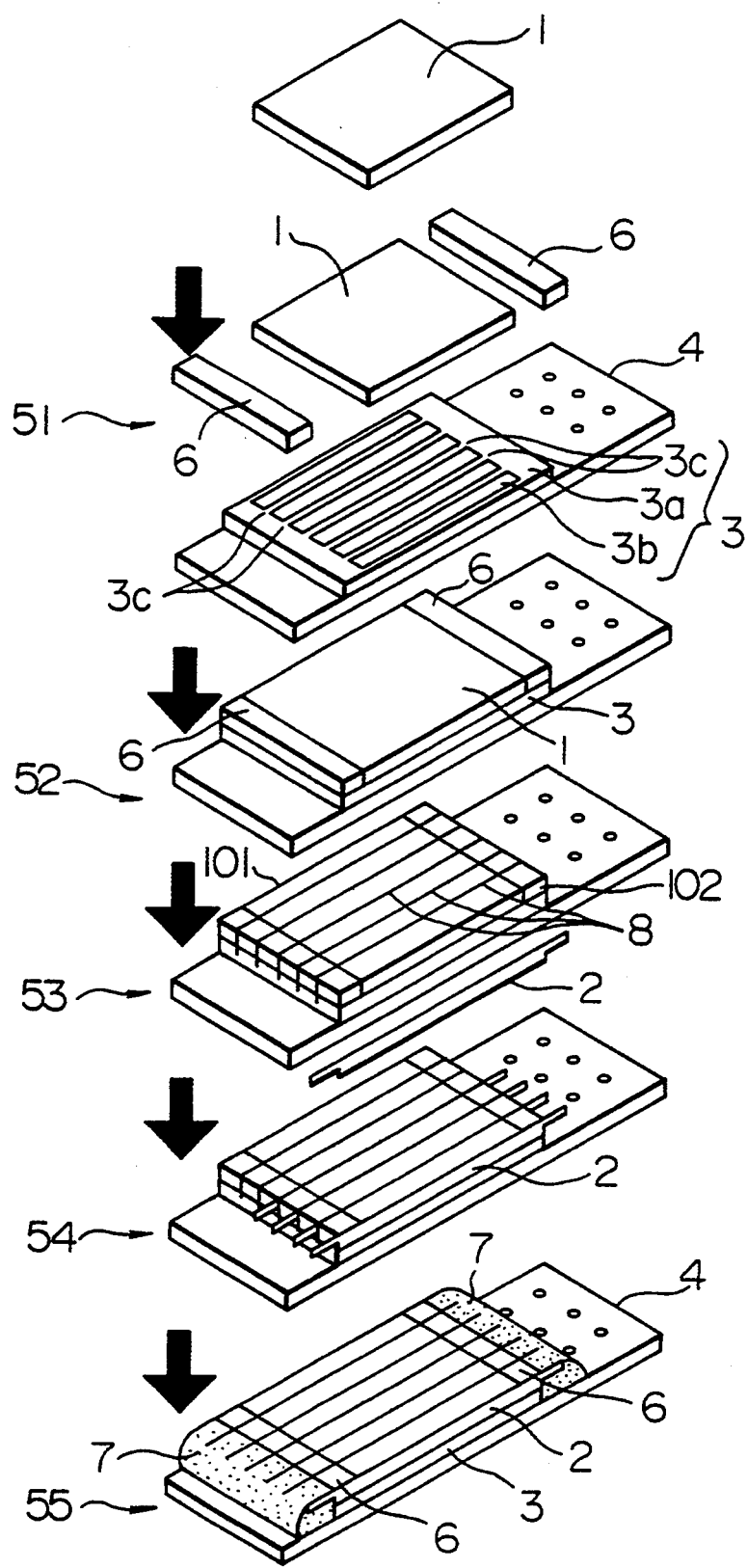
FIG. 1 is a schematic perspective view illustrating the structure of a first embodiment of the radiation detector according to the present invention.

FIG. 1 shows a first embodiment of the radiation detector according to the present invention. Referring to FIG. 1, a pair of light shields 6 each in the form of a solid rectangular strip are precisely cut to have the same width and thickness as those of a scintillator 1 in the form of a plate. In a step 51, these light shields 6 are integrally bonded by an adhesive to both ends respectively of the scintillator 1 located in the direction of groove cutting. Then, in a step 52, the combination of the scintillator 1 and the light shields 6 bonded together is bonded by an adhesive to an upper surface 3a of a multi-channel Si photodiode 3. The scintillator 1 used in the first embodiment may be a single crystal scintillator formed of a material, such as, NaI, CsI, CdWO$_4$, ZnSO$_4$ or BGO or a ceramic scintillator formed of a material, such as, Gd$_2$O$_2$S: Pr or Gd$_2$O$_2$S: Eu. The thickness of the scintillator 1 is commonly 1 mm to 5 mm although it differs depending on the X-ray stopping power of the material used to form the scintillator 1.

Also, the material of the adhesives described above is required to satisfy such conditions that its light reflectivity does not appreciably vary in the light wavelength range (400 nm to 900 nm) of light emitted from the scintillator 1, it has a high degree of transparency, its refractive index is relatively close to that of a light reflection preventive film formed on the surface of light detection parts 3b of the Si photodiode 3, etc. For example, the adhesives used in the first embodiment are preferably an epoxy resin, an acrylic resin or the like.

Each of the solid light shields 6 is formed of a material whose reflectivity does not appreciably vary in both the emission wavelength range of the scintillator 1 and the wavelength sensitivity range (400 nm to 900 nm) of the Si photodiode 3 and which can absorb the greatest possible quantity of light. More concretely, the material of the light shields 6 has such an optical characteristic that its light reflectivity is lower than 30%, and the variation of the reflectivity in the light wavelength range of 400 nm to 900 nm is less than 20%. Especially, it is preferable that the reflectivity of the material is lower than 5%, and the variation of the reflectivity in the above wavelength range is less than 10%. For example, solid graphite, a carbide, a sintered material, such as, ceramics or like material containing a carbide, or a material containing graphite or a carbide is preferably used as the material having the optical characteristic described above. Also, the above material may be a solid prepared by solidifying a black or grayish black pigment in the form of an oxide, such as, OsO, CrO, SnO, TeO, Pb$_2$O, NbO, BiO, MoO or RuO, or a sulfide, such as, FeS, NiS or Mo$_2$S$_3$ by a polymeric resin binder, such as, an epoxy resin, an acrylic resin, a vinyl chloride resin or a styrol resin. Further, a single crystal material, such as, single crystal Si, Ge or the like may be used as the material of the light shields 6.

Then, in a step 53, the combination of the scintillator 1 and the light shields 6 bonded to the upper surface 3a of the Si photodiode 3 is diced or cut by, for example, a dicer to be isolated into individual light detection elements. The dicing operation is made along isolation lines 3c isolating the individual light detection parts 3b patterned by a high precision photomask from the remaining non-light detection parts, and the depth of cutting in this case is 40 µm to 50 µm from the upper surface 3a of the Si photodiode 3. By the above cutting operation, a plurality of grooves 8 for insertion of an isolation plate 2 in each of them are formed.

Then, in a step 54, the isolation plate 2 is inserted into each of the grooves 8 thus formed, and, in a step 55, the isolation plates 2 are fixed at their both ends to the outer ends of the light shields 6 by bonding with an adhesive 7, thereby forming a multi-elements radiation detector in which individual light detection elements are optically isolated from each other.

One side surface 102 of the scintillator 1 is engaged by one isolation plate 2 which is intimately brought into contact and fixed. On the other hand, the other side surface 101 of the scintillator 1 is not engaged by any isolation plate 2.

A plurality of radiation detectors made in the manner described above are arrayed side by side to constitute a radiation detector consisting of a required number of detection elements. In this case, the scintillators 1 are arrayed in such a relation that each of the scintillators 1 is brought into intimate contact at its side surface 101 with the side surface 102 of the adjacent scintillator 1. Also, in this case, the isolation plate 2 is brought into intimate contact with the side surface 101 of the outermost detector of the detector assembly consisting of the unit detectors shown in FIG. 1.

In the unit radiation detector formed by the steps described above, the light shields 6 prevent leakage of light from the ends of the scintillator 1 located in the direction of groove cutting, so that undesirable crosstalk between the adjacent light detection elements can be reliably prevented. Because the scintillator 1 and the light shields 6 are integrally bonded to the upper surface 3a of the Si photodiode 3, and the combination of the scintillator 1 and the light shields 6 is cut into the individual detection elements along the channel isolation lines 3c to be isolated from each other, any relative dimensional difference and position deviation do not occur among the scintillator 1, the light shields 6 and the Si photodiode 3, and the undesirable crosstalk between the adjacent light detection elements can be more reliably prevented.

Also, because undesirable reflection of light at the ends of the scintillator 1 located in the direction of groove cutting can be prevented by the light shields 6, the reflectivities at those ends are controlled to be maintained at the same constant value. Therefore, the prior art tendency of giving rise to fluctuations of the spectral sensitivities of the individual light detection elements attributable to the difference between the reflectivities at those ends can be prevented, so that the possibility of occurrence of an undesirable ring artifact can be minimized.

Further, because the above manner of cutting process can improve both the dimensional precision and the positional precision and can also make uniform those precisions, not only undesirable fluctuations of the optical characteristics of the individual light detection elements can be prevented, but also the detector assembling process requiring the high degree of precision can be dispensed with, thereby improving the industrial productivity of the radiation detector.

Figure 2:
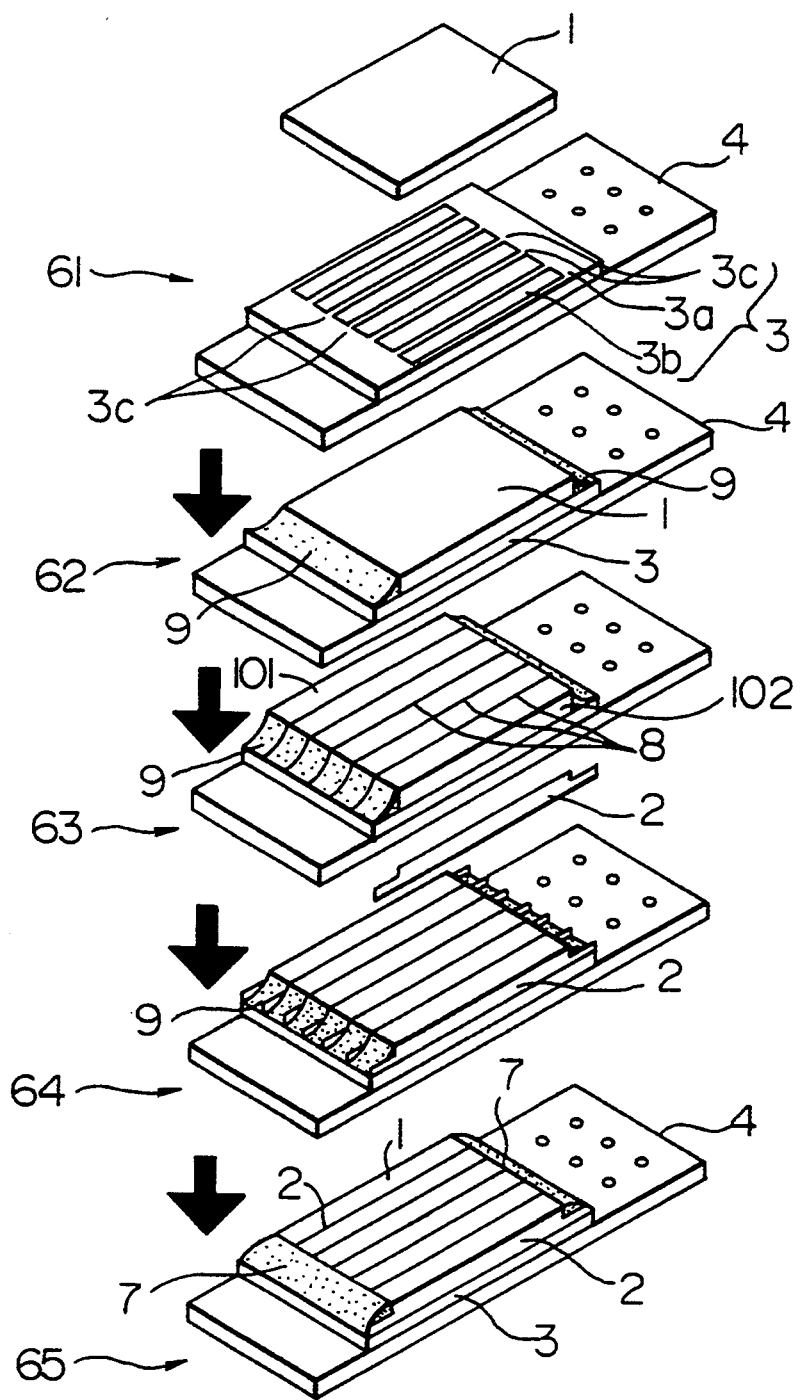
FIG. 2 is a schematic perspective view illustrating the structure of a second embodiment of the radiation detector according to the present invention.

FIG. 2 shows a second embodiment of the radiation detector according to the present invention, and, in FIG. 2, like reference numerals are used to designate like parts appearing in FIG. 1. Referring to FIG. 2, a light shield 9 in the form of a layer is coated on each of the ends of a scintillator 1 in the form of a plate located in the direction of groove cutting in lieu of the solid light shields 6 shown in FIG. 1. That is, as in the case of FIG. 1, the scintillator 1 in plate form is first bonded to an upper surface 3a of a Si photodiode 3 in a step 61, and the light shields 9 in layer form are then coated on the respective ends of the scintillator 1 located in the direction of groove cutting in a step 62.

The material of the light shields 9 has the same optical characteristic as that of the material of the solid light shields 6 shown in FIG. 1. More concretely, the material is a powdery black or grayish black substance whose reflectivity does not appreciably vary in a light wavelength range of 400 nm to 900 nm and which can absorb the greatest possible quantity of light. For example, the material of the light shields 9 is prepared by mixing carbon, a carbide, an oxide, such as, OsO, CrO, SnO, TeO, $Pb_2O$, NbO, BiO, MoO or RuO, or a sulfide, such as, FeS, NiS, or $Mo_2S_3$ into a polymeric resin, such as, an epoxy resin, an acrylic resin or a styrol resin.

After the coated light shields 9 are cured, isolation grooves 8 similar to those shown in FIG. 1 are formed in a step 63, and isolation plates 2 are inserted into those isolation grooves 8 respectively in a step 64. Then, the isolation plates 2 are fixed at their both ends to the light shields 9 by bonding with an adhesive 7 in a step 65, thereby forming a multi-elements radiation detector in which the individual light detection elements are optically isolated from each other.

The side surfaces 101 and 102 of the scintillator 1 are processed as in the case of FIG. 1.

In this second embodiment, the solid light shields 6 need not be prepared beforehand, and the step of bonding these light shields 6 to the scintillator 1 is unnecessary. Therefore, the second embodiment is advantageous over the first embodiment in that the number of required parts as well as the number of required steps can be decreased while exhibiting the same function and effects as those of the first embodiment.

Figure 3:
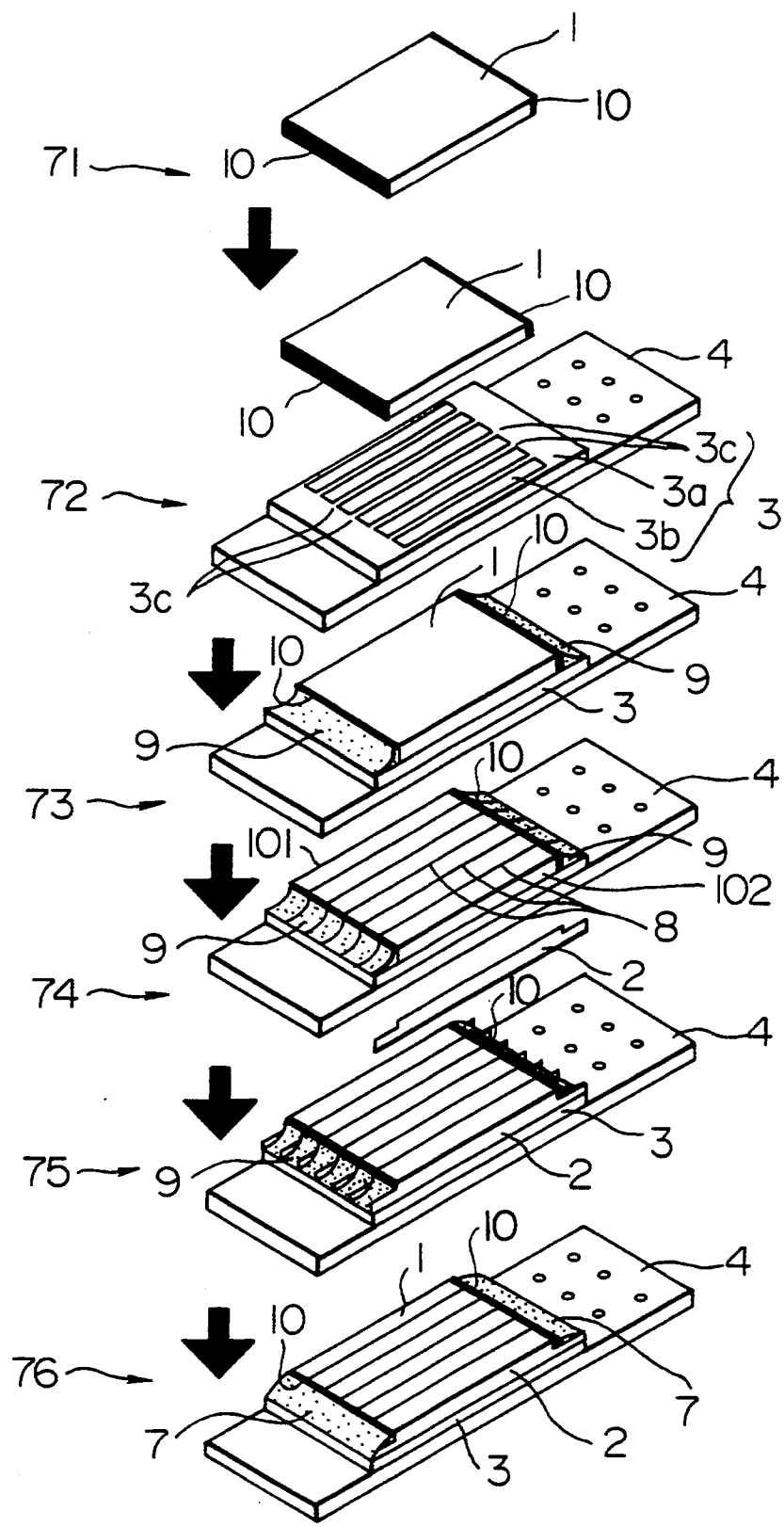
FIG. 3 is a schematic perspective view illustrating the structure of a third embodiment of the radiation detector according to the present invention.
Figure 4:
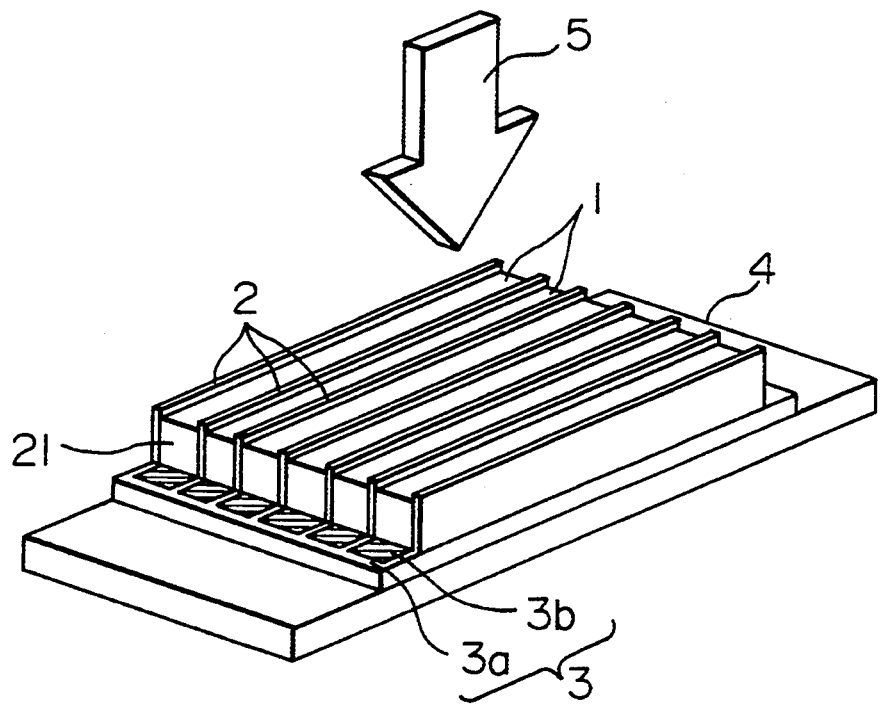
FIG. 4 is a schematic perspective view showing the basic structure of a prior art X-ray detector of multi-element solid type.

FIG. 3 shows a third embodiment of the radiation detector according to the present invention, and, in FIG. 3, like reference numerals are used to designate like parts appearing in FIG. 2. Referring to FIG. 3, a scintillator 1 is in the form of a plate, and a light shield 10 in the form of a resin is coated beforehand on each of both ends of the scintillator 1 located in the direction of groove cutting in a step 71. The same resin as that used in the second embodiment is also used in this third embodiment. However, a silk printing ink commercially available in the market may be used.

As in the cases of the first and second embodiments, the scintillator 1 coated with the light shields 10 is bonded to an upper surface 3a of a Si photodiode 3 in a step 72. Then, as in the case of the second embodiment, a light shield 9 is coated in a step 73 on the light shield 10 covering each of the both ends of the scintillator 1 located in the direction of groove cutting. Also, as in the case of the second embodiment, isolation grooves 8 are formed in a step 74, and isolation plates 2 are inserted into the isolation grooves 8 respectively in a step 75. Then, the isolation plates 2 are bonded at their ends to the light shields 9 by an adhesive 7, thereby forming a multi-elements radiation detector in which the individual light detection elements are optically isolated from each other.

In this third embodiment, the light shields 10 are coated beforehand on the flat and smooth end surfaces of the scintillator 1. Therefore, the third embodiment is advantageous in that not only the step of coating the light shields 9 is facilitated as compared to the second embodiment, but also an undesirable trouble, such as, intrusion of bubbles into the light shielded surfaces of the scintillator 1 can be more reliably prevented.

The side surfaces 101 and 102 of the scintillator 1 are processed as in the case of the first embodiment shown in FIG. 1.

We claim:

1. A radiation detector comprising:
   a multi-channel photodiode formed on a substrate and having individual channels isolated from each other by a plurality of channel isolation lines respectively;
   a scintillator having at least two ends and cut along said isolation lines to be formed with a plurality of grooves in which a plurality of isolation plates isolating said channels respectively are inserted; and
   light shielding means coated on or bonded to the at least two ends of said scintillator located in the direction of groove cutting, said light shielding means having a light absorption factor which is greater than a light reflection factor thereof.

2. A radiation detector according to claim 1, wherein said light shielding means is formed of a material having an optical characteristic in which the reflectivity is lower than 30%, and the variation of said reflectivity in a light wavelength range of 400 nm to 900 nm is less than 20%.

3. A radiation detector according to claim 1, wherein said light shielding means is formed of a material containing graphite or a carbide.

4. A radiation detector according to claim 3, wherein said material containing said carbide is a ceramic material.

5. A radiation detector according to claim 1, wherein said light shielding means is formed of a polymeric resin material containing graphite or a polymeric resin material in which a pigment containing a carbide is mixed.

6. A method for making a radiation detector comprising the steps of:
  bonding light shielding means to at least two ends of a plate-form scintillator located in a direction of groove cutting of isolation plate insertion grooves, said light shielding means having a light absorption factor which is greater than a light reflection factor thereof;
  bonding said plate-form scintillator having said light shielding means bonded thereto to an upper surface of a multi-channel photodiode;
  forming isolation plate insertion grooves on all of said light shielding means, said scintillator and said photodiode along channel isolation lines isolating individual channels of said photodiode from each other;
  inserting isolation plates into said isolation plate insertion grooves respectively; and
  fixing said isolation plates to the at least two ends of said scintillator by bonding with an adhesive.

7. A method for making a radiation detector according to claim 6, wherein said light shielding means is formed of a material having an optical characteristic in which the reflectivity is lower than 30%, and the variation of said reflectivity in a light wavelength range of 400 nm to 900 nm is less than 20%.

8. A method for making a radiation detector according to claim 6, wherein said light shielding means is formed of a material containing graphite or a carbide.

9. A method for making a radiation detector according to claim 8, wherein said material containing said carbide is a ceramic material.

10. A method for making a radiation detector according to claim 6, wherein said light shielding means is formed of a polymeric resin material containing graphite or a polymeric resin material in which a pigment containing a carbide is mixed.

11. A method for making a radiation detector comprising the steps of:
  bonding a scintillator in plate form to an upper surface of a multi-channel photodiode;
  coating light shielding means in resin form on at least two ends of said scintillator located in a direction of groove cutting of isolation plate insertion grooves, said light shielding means having a light absorption factor which is greater than a light reflection factor thereof;
  after said light shielding means is cured, forming isolation plate insertion grooves on all of said light shielding means, said scintillator and said photodiode along channel isolation lines isolating individual channels of said photodiode from each other;
  inserting isolation plates into said isolation plate insertion grooves respectively; and
  fixing said isolation plates to the at least two ends of said scintillator by bonding with an adhesive.

12. A method for making a radiation detector according to claim 11, wherein said light shielding means is formed of a material having an optical characteristic in which the reflectivity is lower than 30%, and the variation of said reflectivity in a light wavelength range of 400 nm to 900 nm is less than 20%.

13. A method for making a radiation detector according to claim 11, wherein said light shielding means is formed of a material containing graphite or a carbide.

14. A method for making a radiation detector according to claim 13, wherein said material containing said carbide is a ceramic material.

15. A method for making a radiation detector according to claim 11, wherein said light shielding means is formed of a polymeric resin material containing graphite or a polymeric resin material in which a pigment containing a carbide is mixed.

16. A method for making a radiation detector comprising the steps of:
  coating first light shielding means on at least two ends of a plate-form scintillator located in a direction of groove cutting of isolation plate insertion grooves, said light shielding means having a light absorption factor which is greater than a light reflection factor thereof;
  bonding said plate-form scintillator to an upper surface of a multi-channel photodiode;
  coating resin-form second light shielding means on the at least two ends of said scintillator in the direction of groove cutting;
  after said second light shielding means is cured, forming isolation plate insertion grooves on all of said light shielding means, said scintillator and said photodiode along channel isolation lines isolating individual channels of said photodiode from each other;
  inserting isolation plates into said isolation plate insertion grooves respectively; and
  fixing said isolation plates to the at least two ends of said scintillator by bonding with an adhesive.

17. A method for making a radiation detector according to claim 16, wherein said first and second light shielding means are formed of a material having an optical characteristic in which the reflectivity is lower than 30%, and the variation of said reflectivity in a light wavelength range of 400 nm to 900 nm is less than 20%.

18. A method for making a radiation detector according to claim 16, wherein said first and second light shielding means are formed of a material containing graphite or a carbide.

19. A method for making a radiation detector according to claim 18, wherein said material containing said carbide is a ceramic material.

20. A method for making a radiation detector according to claim 16, wherein said first and second light shielding means are formed of a polymeric resin material containing graphite or a polymeric resin material in which a pigment containing a carbide is mixed.

* * * * *